(12) United States Patent
Ravikumar

(10) Patent No.: US 7,326,230 B2
(45) Date of Patent: Feb. 5, 2008

(54) VASCULAR SEALING DEVICE AND METHOD OF USE

(76) Inventor: Sundaram Ravikumar, 265 Hardscrabble Rd., Briarcliff Manor, NY (US) 10510

( * ) Notice: Subject to any disclaimer, the term of this patent is extended or adjusted under 35 U.S.C. 154(b) by 752 days.

(21) Appl. No.: 10/692,027

(22) Filed: Oct. 23, 2003

(65) Prior Publication Data

US 2005/0090859 A1    Apr. 28, 2005

(51) Int. Cl.
A61B 17/08     (2006.01)
A61D 1/00      (2006.01)
(52) U.S. Cl. .................... 606/213; 606/198; 606/217
(58) Field of Classification Search ............... 606/198, 606/213, 215, 216, 217, 218, 113, 114, 127
See application file for complete search history.

(56) References Cited

U.S. PATENT DOCUMENTS

| 4,744,364 A | 5/1988 | Kensey ................ 128/334 |
| 4,890,612 A | 1/1990 | Kensey ................ 606/213 |
| 5,021,059 A | 6/1991 | Kensey et al. ........ 606/213 |
| 5,350,399 A * | 9/1994 | Erlebacher et al. ... 606/213 |
| 5,674,231 A | 10/1997 | Green et al. ......... 606/142 |
| 5,746,755 A | 5/1998 | Wood et al. .......... 606/148 |
| 6,171,329 B1 | 1/2001 | Shaw et al. .......... 606/213 |
| 6,447,524 B1 * | 9/2002 | Knodel et al. ....... 606/151 |
| 6,547,806 B1 | 4/2003 | Ding ................... 606/213 |
| 6,749,622 B2 * | 6/2004 | McGuckin et al. .... 606/213 |
| 6,949,107 B2 * | 9/2005 | McGuckin et al. .... 606/142 |

OTHER PUBLICATIONS

"Perclose A-T Simplifies Vessel Closure After Cardiac Catherterization Procedures" Article dated: Nov. 20, 2002 (Abbott Park, IL).
"Hemostatic Device" Article from HeartCenter Online.
"A Patient's Guide to Questions & Ansers about Vascular Sealing", Vascular Sol. 2002.
"VasoSeal ED Procedure" (New Arterial Locater Technology Provides and Easier, Surer Method of Locating the Femoral Artery Puncture) from Datascope, 2001.

* cited by examiner

Primary Examiner—Michael J. Hayes
Assistant Examiner—Michael Mendoza
(74) Attorney, Agent, or Firm—Gordon & Jacobson, PC

(57) ABSTRACT

An improved device for closing an opening in a blood vessel includes a cannula holding a first wire group, a second wire group, and a wire fixation device. The positions of the first wire group and second wire group are independently adjustable. The first wire group is deployed from the cannula into an interior region of the blood vessel and retracted to a desired position in contact with an intimal surface of the blood vessel around the opening. The second wire group is deployed from the cannula and moved to a desired position in contact with an adventitial surface of the blood vessel around the opening. The fixation device is adapted to affix the first and second wire groups in their desired positions to thereby effectuate closure of the opening in the blood vessel.

12 Claims, 3 Drawing Sheets

VASCULAR SEALING DEVICE AND METHOD OF USE

BACKGROUND OF THE INVENTION

1. Field of the Invention

This invention relates generally to medical devices. More particularly, this invention relates to hemostatic devices used to seal blood vessel punctures or incisions.

2. State of the Art

A wide variety of intravascular procedures involve the insertion of various medical instruments, such as catheters and other surgical instruments and devices, into an artery. For example, in the treatment of vascular disease, balloon catheters and the like are typically inserted into the artery to perform procedures therein. To carry out such procedures, an opening is generally formed in the affected artery or at a peripheral location (such as the femoral artery).

After the procedure has been completed, bleeding through the arterial opening must be stopped. Traditional methods for closing the arterial opening involve sutures, clamps and/or the application of prolonged manual pressure to the puncture site. Alternative devices have been proposed. For example, U.S. Pat. No. 6,547,806 to Ding describes the use of a collapsible sealing member including a fluid-impervious film carried by a shape-resilient wire structure. The sealing member is housed within a sheath. The sheath (and the sealing member therein) are inserted to/through the arterial opening, and the sealing member is deployed from within the sheath into the interior region of the artery. During deployment, the sealing member expands into its naturally expanded configuration. The sealing member is then securely positioned against the inner wall of the artery adjacent the opening in the artery. Sealant (in flowable form, gel, solid, or paste) is then delivered to the tissue leading to the arterial opening. Depending upon the sealant used, it is necessary to wait a period of time (or provide appropriate light for a photo-initiated material) before the sealant forms a hemostatic closure. When the sealant is ready, the sealing member is removed from the artery by repositioning the sealing member back into the sheath, and retracting the sheath (and sealing member therein) from the artery through the sealant. A small opening may remain along the path where the device is withdrawn. Compression or a surgical suture may be used to close this small opening. This device has numerous drawbacks, including the wait-time (or the additional steps) required for the sealant to form a hemostatic closure as well as the delay and associated problems in closing the small opening that remains upon withdrawal of the device.

Another device is described in U.S. Pat. No. 6,171,329 to Shaw et al. It includes a distal sealing membrane and proximal sealing membrane disposed within a delivery catheter. Both sealing membranes are formed from a single elastic wire shaped into two helical support structures with an eyelet therebetween. Multiple layers of a PTFE film are formed on the two helical support structures. Deployment of the device is accomplished by inserting the delivery catheter with the two sealing members therein through the tissue opening and forcing the distal sealing member out of the delivery catheter to enable the distal sealing member to expand to its deployed shape. The delivery catheter is then withdrawn from the tissue opening, and the proximal sealing member is forced out of the delivery catheter to enable the proximal sealing member to expand to its deployed shape. A latch portion of the wire is used to secure the two sealing members in place. This device has numerous drawbacks. For example, because the device is formed from a single wire, the positions of the two sealing members relative to one another are fixed. Thus, it cannot readily conform to (and seal) tissue openings of varying wall thickness. Moreover, the operator manipulates the single wire in deploying both the distal sealing member and the proximal sealing member and thus risks inadvertent retraction of the distal sealing member through the tissue opening and damage thereto.

Thus, there remains a need in the art for an improved hemostatic closure device that provides for efficient and effective closures of vascular openings in arteries or other blood vessels.

SUMMARY OF THE INVENTION

It is therefore an object of the invention to provide an improved hemostatic closure device that provides for efficient and effective closure of a vascular opening.

It is another object of the invention to provide an improved hemostatic closure device that provides for efficient and effective closure of vascular openings with variable wall thicknesses.

It is a further object of the invention to provide an improved hemostatic closure device that provides for effective closure of a vascular opening with minimal delay associated therewith.

In accord with these objects, which will be discussed in detail below, an improved device for closing an opening in a blood vessel includes a cannula holding a first wire group, a second wire group, and a wire fixation device. The positions of the first wire group and second wire group are independently adjustable. The first wire group is deployed from the cannula into an interior region of the blood vessel and retracted to a desired position in contact with an intimal surface of the blood vessel around the opening. The second wire group is deployed from the cannula and moved to a desired position in contact with an adventitial surface of the blood vessel around the opening. The fixation device is adapted to affix the first and second wire groups in their desired positions to thereby effectuate closure of the opening in the blood vessel.

It will be appreciated that the improved vascular closure device provides for effective closure of a vascular opening with minimal delay associated therewith, and is suitable for use in conjunction with blood vessels of varying wall thickness.

According to one embodiment of the invention, the fixation device comprises a lock bead having a passageway through which pass the first and second wire groups.

According to another embodiment of the invention, the first and second wire groups assume different configurations when deployed from the cannula. Preferably, these different configurations include distal portions of the first and second wire groups having a substantially planar shape that is orthogonally disposed with respect to a longitudinal axis of the cannula.

In yet another embodiment of the present invention, the first and second wire groups are formed from a metal, such as a metal alloy (and most preferably from an elastic shape memory alloy such as nitinol or ELGILOY).

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
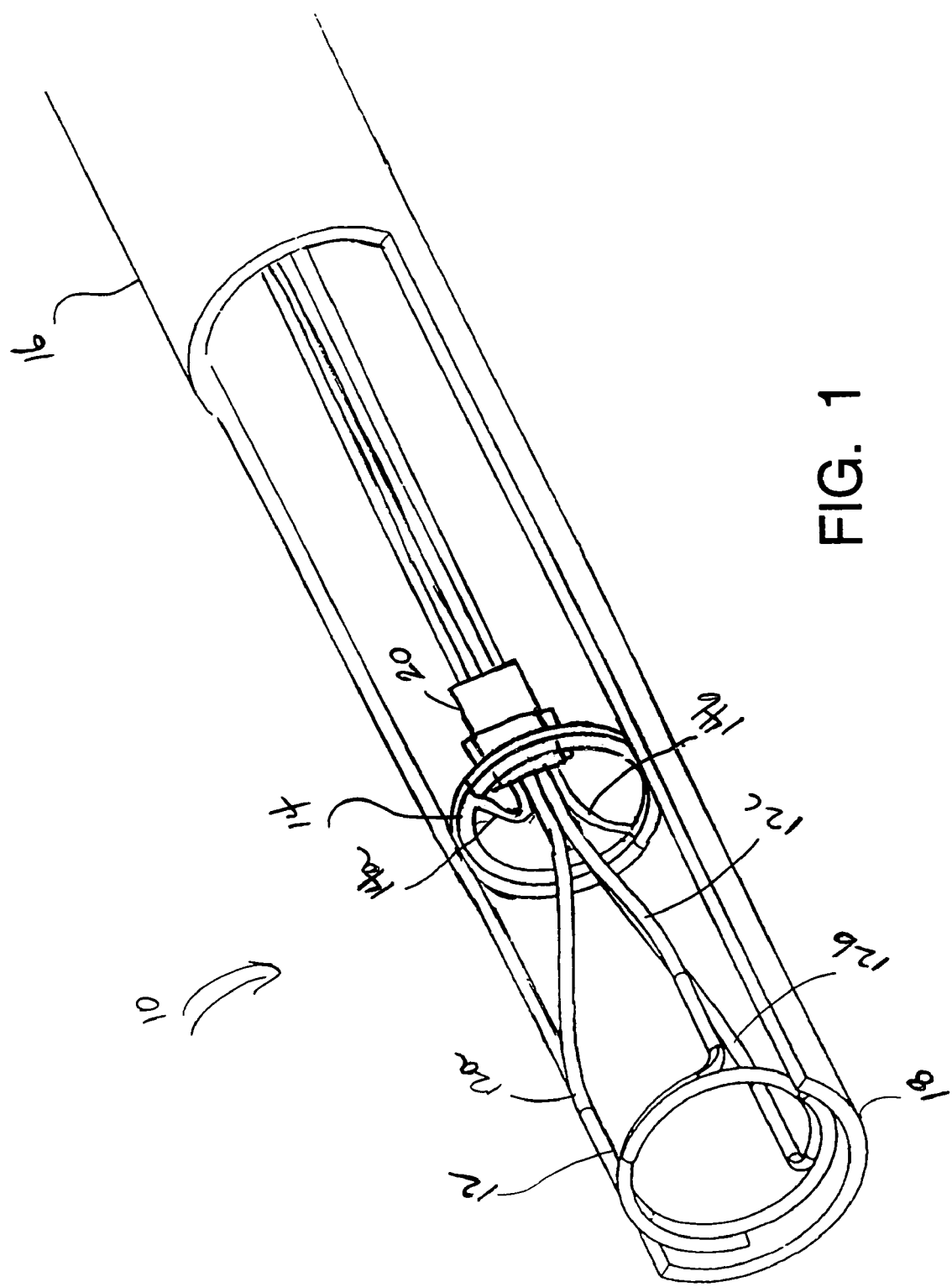
FIG. 1 is a schematic illustration of a vascular closure device in accordance with the present invention, with a portion of the cannula cut-away to illustrate the components housed therein.

Turning now to FIG. 1, there is shown a vascular closure device 10 in accordance with the present invention. This device 10 generally includes two resilient wire groups referred to herein as the intimal wire group 12 and the adventitial wire group 14. Both wire groups 12, 14 are collapsible for storage in a cannula 16 as shown, and move inside the cannula 16 toward its distal end 18 for deployment therefrom. When deployed from the distal end 18 of the cannula 16 (see FIGS. 2 and 3), the distal portions of the intimal wire group 12 and adventitial wire group 14 naturally change shape into a configuration suitable for closing the opening in a blood vessel. In addition, the device 10 includes a fixation device 20, which is used to lock the intimal wire group 12 and adventitial wire group 14 together such that they cannot move relative to one another as described below in more detail. The fixation device 20 also preferably contributes to coaxial alignment of the intimal wire group 12 and adventitial wire group 14 during deployment. In the preferred embodiment of the present invention, the fixation device 20 is realized by a lock bead which provides a passageway through which slides both the intimal wire group 12 and adventitial wire group 14.

When stored in the cannula 16, the distal portion of the intimal wire group 12 is positioned closer to distal end 18 of the cannula 16 than is the distal portion of the adventitial wire group 14. This positioning enables deployment of the intimal wire group 12 from the distal end 18 of the cannula 16 first, followed by deployment of the adventitial wire group 14 from the distal end 18 of the cannula 16.

The device 10 also includes a wire advancement mechanism (not shown) that enables the operator to independently adjust the position of the intimal wire group 12 and adventitial wire group 14 along the longitudinal axis of cannula 16. This mechanism is manipulated by the operator to slide the intimal wire group 12 and adventitial wire group 14 toward the distal end 18 of the cannula 16 for deployment therefrom. The wire advancement mechanism may be realized by two cylindrical structures, one inside the other that slide relative to one another. The outer cylinder buts up against the distal portion of the intimal wire group 12. The inner cylinder buts up against the fixation device 20. Advancement of intimal wire group 12 toward the distal end 18 of the cannula 16 is provided by sliding the outer cylinder along longitudinal axis of cannula 16 toward its distal end 18. Advancement of adventitial wire group 14 toward the distal end 18 of the cannula 16 is provided by sliding the inner cylinder along longitudinal axis of cannula 16 toward its distal end 18. In this configuration, the outer cylinder encompasses the adventitial wire 14 group and fixation device 20 at certain parts of the deployment sequence (for example, when the intimal wire group 12 is being deployed). Alternatively, the wire advancement mechanism may be realized by two projections (or other mechanical structures) that are affixed to (or grip) the proximal ends of the two wire groups 12, 14 (or to wire portions attached thereto). In this configuration, advancement of intimal wire group 12 is provided by movement of its corresponding structure along longitudinal axis of cannula 16 toward its distal end 18, and advancement of adventitial wire group 14 is provided by movement of its corresponding structure along longitudinal axis of cannula 16 toward its distal end 18.

The wire groups 12, 14 can be formed of any suitable resilient material. For example, various metals, such as metal alloys (including elastic shape memory alloys such as nitinol or ELGILOY) or stainless steel, may be used. Alternatively, polymeric material may be used. In addition, the intimal wire group 12 can be coated with a drug eluding material which dissolves when in contact with blood in the vessel. Moreover, it is contemplated that hemostatic material (such as a hemostatic gel or gel-foam, or SURGICEL material commercially available from Johnson and Johnson) can be integrated with the adventitial wire group 14 in order to provide enhanced hemostatic closure of the vessel opening.

Figure 2:
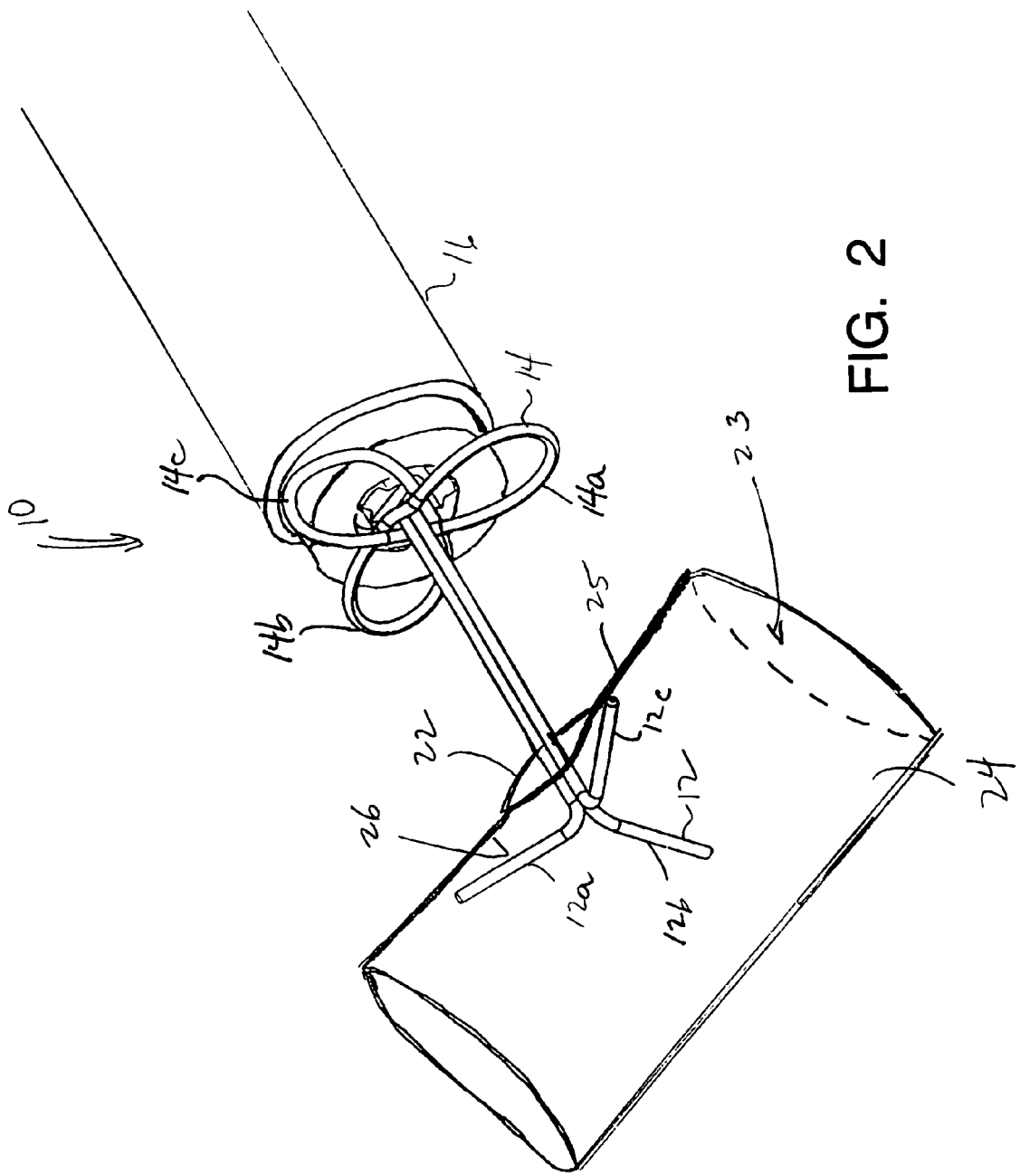
FIG. 2 is a schematic illustration of a vascular closure device in accordance with the present invention, with the intimal wire group deployed inside the blood vessel in accordance with the present invention.
Figure 3:
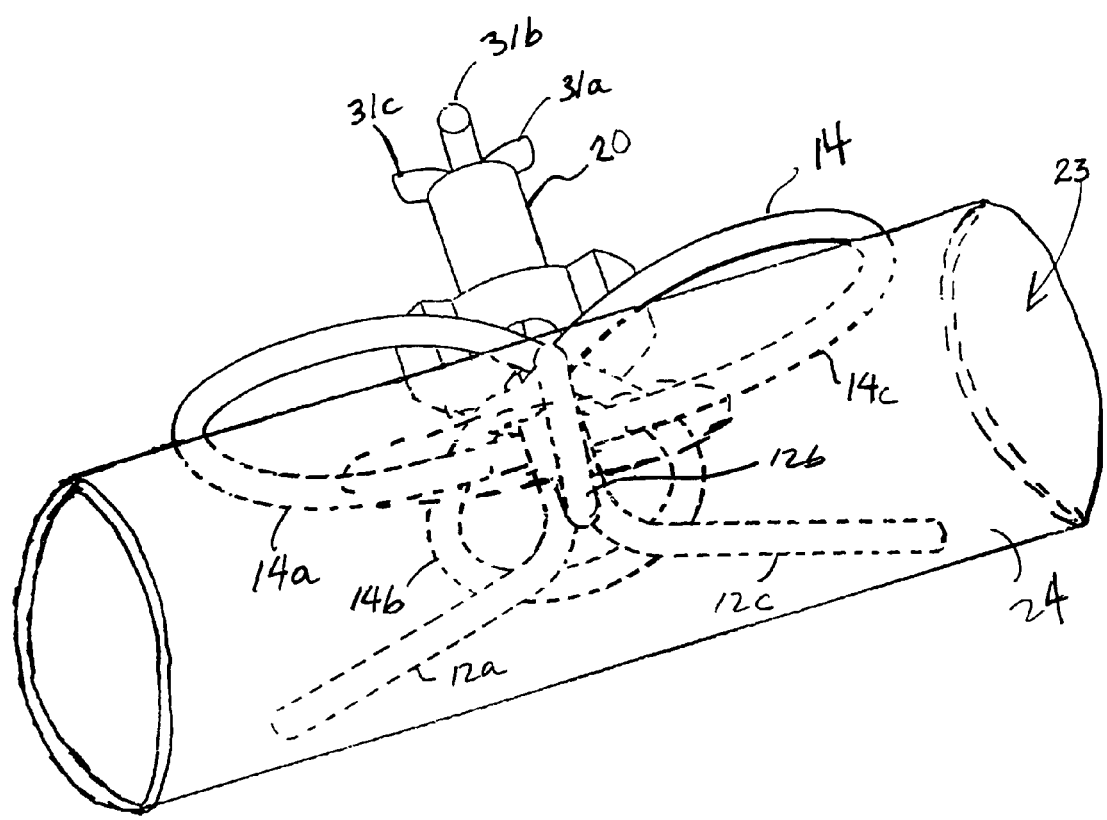
FIG. 3 is a schematic illustration of the vascular closure device of the present invention, with the intimal wire group and adventitial wire group positioned on opposite surfaces of the vessel wall around the opening in accordance with the present invention.

In the embodiments illustrated in FIGS. 1-3, the intimal wire group 12 and adventitial wire group 14 change shape when deployed from the cannula 16 such that the distal portions of the two wire groups 12, 14 are substantially planar in shape and orthogonally disposed with respect to the longitudinal axis of the cannula 16. For example, in the embodiments shown, the intimal wire group 12 includes three wires 12a, 12b, 12c. When stored in the cannula 16, the distal portions of the three wires 12a, 12b, 12c have substantially planar circular configurations as shown in FIG. 1. The radii of such circular configurations are orthogonally disposed with respect to the longitudinal axis of the cannula 16. When deployed from the cannula 16, the distal portions of the three wires 12a, 12b, 12c naturally change shape such that three wires 12a, 12b and 12c protrude from longitudinal axis of the cannula 16 radially outward in a plane as shown in FIG. 2. Similarly, the adventitial wire group 14 includes three wires 14a, 14b, 14c. When stored in the cannula 16, the distal portions of the three wires 14a, 14b, 14c have substantially planar circular configurations as shown in FIG. 1. The radii of such circular configurations are orthogonally disposed with respect to the longitudinal axis of the cannula 16. When deployed from the cannula 16, the distal portions of the three wires 14a, 14b, 14c naturally change shape such that three wires 14a, 14b and 14c protrude from longitudinal axis of the cannula 16 radially outward in three distinct loops as shown in FIG. 2. The three loops 14a, 14b, and 14c lie in a common plane that is substantially orthogonal to the longitudinal axis of the cannula 16 as shown. Alternatively, the distal portions of the intimal wire group 12 and the adventitial wire group 14 may assume any other arbitrary shape (such as frusto-conical shapes, spherical (or spheroid sectional) shapes, etc.).

In the preferred method of the present invention, the cannula 16 (which has an inside opening diameter typically between 5 french and 12 french) is inserted into (and possibly through) the vascular opening 22 that is to be closed. The intimal wire group 12 is then advanced toward the distal end 18 of the cannula 16 such that it is deployed in the interior region of the lumen 23 of blood vessel 24 (see FIG. 2). During deployment of the intimal wire group 12, the adventitial wire group 14 remains inside the cannula 16. Next, the cannula 16 is retracted through the vascular opening 22 while the intimal wire group 12 remains positioned in the interior region of the lumen 24. The adventitial wire group 14 is advanced toward the distal end 18 of the cannula 16 such that it is deployed (see FIG. 2) and then positioned in contact to the adventitial surface 25 around the opening 22. In conjunction with the deployment and advancement of the adventitial wire group 14, the intimal wire group 12 is retracted such that it comes in contact to the intimal surface 26 around the opening 22. When both wire groups 12, 14 are in contact with the opposing surfaces 25, 26, the operator locks the position of the two wire groups with the fixation device 20. In the preferred embodiment, the fixation device 20 is realized by a lock bead that affixes the positions of the two wire groups by positioning the lock bead snuggly against the distal portion of the adventitial wire group 14, cutting the wires of both wire groups 12, 14 leaving ends (three shown 31*a*, 31*b*, 31*c*) that protrude from the lock bead, and bending these ends (31*a*, 31*b*, 31*c*) back in distal direction around lock bead as shown in FIG. 3. With both wire groups 12, 14 affixed in contact with the opposing surfaces 25, 26, the wire surfaces substantially block the flow of blood through the vessel opening. As described above, it is contemplated that the adventitial wire group 14 may include hemostatic material integral thereto. In this configuration, the hemostatic material aids in blocking the flow of blood through the vessel opening to provide hemostatic closure of the opening.

There have been described and illustrated herein several embodiments of a vascular closure device and corresponding method of operation. While particular embodiments of the invention have been described, it is not intended that the invention be limited thereto, as it is intended that the invention be as broad in scope as the art will allow and that the specification be read likewise. Thus, while particular resilient materials have been disclosed, it will be appreciated that other resilient materials can be used as well. In addition, while particular shapes and configurations of wire-based closure devices have been disclosed, it will be understood that other shapes and configurations can be used. Furthermore, while a particular wire fixation device is disclosed, it will be understood that other wire fixation devices can be similarly used. It will therefore be appreciated by those skilled in the art that yet other modifications could be made to the provided invention without deviating from its spirit and scope as claimed.

What is claimed is:

1. A device for closing an opening in a blood vessel comprising:

a) a cannula;

b) a first wire group assuming a first shape in said cannula;

c) a second wire group assuming a second shape in said cannula; and d) a wire fixation device operably coupled to said first and second wire groups;

wherein positions of said first wire group and said second wire group are independently adjustable, said first wire group is deployable from said cannula into an interior region of the blood vessel whereby said first wire group assumes a third shape different from said first shape, said first wire group is retractable to a desired position in contact with an intimal surface of the blood vessel around the opening, said second wire group is deployable from said cannula whereby said second wire group assumes a fourth shape different from said second shape, said second wire group is movable to a desired position in contact with an adventitial surface of the blood vessel around the opening, and said fixation device is deployable from said cannula and is adapted to affix said first and second wires in their desired positions to thereby effectuate closure of the opening in the blood vessel.

2. The device according to claim 1, wherein:
said fixation device comprises a lock bead having a passageway though which pass said first wire group and said second wire group.

3. The device according to claim 2, wherein:
said lock bead is positioned adjacent a distal portion of said second wire group, and said first and second wire groups have sections that protrude proximally from said lock bead, wherein said sections are cut and bent back toward their distal ends to affix the positions of said first and second wire groups relative to one another.

4. The device according to claim 1, wherein:
said first and second wire groups assume different configurations when deployed from said cannula.

5. The device according to claim 4, wherein:
said different configurations include distal portions of said first and second wire groups having a substantially planar shape.

6. The device according to claim 5, wherein:
said distal portions are orthogonally disposed with respect to a longitudinal axis of said cannula.

7. The device according to claim 1, wherein:
said first and second wires are formed from a metal.

8. The device according to claim 7, wherein:
said metal comprises a metal alloy.

9. The device according to claim 8, wherein:
said metal alloy comprises an elastic shape memory alloy.

10. The device according to claim 9, wherein:
said elastic shape memory alloy comprises one of nitinol and ELGILOY.

11. The device according to claim 7, wherein:
said metal comprises stainless steel.

12. The device according to claim 1, wherein:
said first and second wires are formed from a polymeric material.

* * * * *